United States Patent
Hotier et al.

(10) Patent No.: US 7,582,208 B2
(45) Date of Patent: *Sep. 1, 2009

(54) PROCESS AND DEVICE FOR SIMULATED MOVING BED SEPARATION WITH A REDUCED NUMBER OF VALVES AND LINES

(75) Inventors: Gerard Hotier, Rueil Malmaison (FR); Philibert Leflaive, Mions (FR); Sylvain Louret, Lyons (FR); Frederic Aügier, Saint Symphorien d Ozon (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/073,697

(22) Filed: Mar. 7, 2008

(65) Prior Publication Data

US 2008/0237132 A1    Oct. 2, 2008

(30) Foreign Application Priority Data

Mar. 9, 2007    (FR) .................................. 07 01772

(51) Int. Cl.
*B01D 15/08* (2006.01)
(52) U.S. Cl. .................................... 210/198.2; 210/659
(58) Field of Classification Search ................. 210/635, 210/656, 659, 662, 198.2
See application file for complete search history.

(56) References Cited

U.S. PATENT DOCUMENTS

| | | | |
|---|---|---|---|
| 4,434,051 A | 2/1984 | Golem | |
| 5,705,061 A * | 1/1998 | Moran | 210/198.2 |
| 5,882,523 A * | 3/1999 | Hotier et al. | 210/659 |
| 5,972,224 A * | 10/1999 | Hotier et al. | 210/659 |

(Continued)

FOREIGN PATENT DOCUMENTS

EP    0 818 226 A1    1/1998

(Continued)

OTHER PUBLICATIONS

French Search Report conducted Nov. 7, 2007 of French Patent Application No. FR 0701772, FA 694565.

*Primary Examiner*—Ernest G Therkorn
(74) *Attorney, Agent, or Firm*—Millen, White, Zelano & Branigan, P.C.

(57) ABSTRACT

The invention concerns a simulated moving bed adsorption separation device comprising a limited number of valves. According to the invention, the device comprises a column with a plurality of sectors Sk with 2 superimposed plates Pi with a single distribution network, each sector Sk comprising an external principal bypass line Lk connected to each plate Pi of Sk via a plate valve $V_i$. Each line Lk comprises a flow limitation means and is connected to each of the fluid networks via a single valve.

Further, the connectors of lines Lk onto the column are offset by at most 20° inside Sk to limit the volume of lines Lk, and are offset by a mean angle in the range 70° to 110° between two neighbouring sectors Sk and Sk+1 so as not to weaken the column mechanically. The plates preferably comprise panels DMEi,j with parallel segments the direction of which varies from plate to plate or per group of 2 plates.

The invention also concerns a separation process using said device, in particular to separate para-xylene or meta-xylene from an aromatic C8 cut.

11 Claims, 7 Drawing Sheets

U.S. PATENT DOCUMENTS

| | | | |
|---|---|---|---|
| 6,017,448 A * | 1/2000 | Hotier et al. ............. | 210/198.2 |
| 6,093,317 A * | 7/2000 | Capelle et al. ........... | 210/198.2 |
| 6,146,537 A * | 11/2000 | Ferschneider et al. ....... | 210/659 |
| 6,149,874 A | 11/2000 | Hotier | |
| 6,156,197 A * | 12/2000 | Dessapt et al. ........... | 210/198.2 |
| 6,224,762 B1 * | 5/2001 | Ferschneider et al. .... | 210/198.2 |
| 6,261,458 B1 | 7/2001 | Callebert et al. | |
| 6,402,959 B1 * | 6/2002 | Dessapt et al. .............. | 210/656 |
| 6,454,948 B2 * | 9/2002 | Ferschneider et al. ....... | 210/659 |
| 6,537,451 B1 * | 3/2003 | Hotier ..................... | 210/198.2 |
| 6,797,175 B2 * | 9/2004 | Hotier ........................ | 210/659 |
| 7,288,200 B1 * | 10/2007 | Hotier et al. ................ | 210/659 |
| 2001/0008220 A1 * | 7/2001 | Ferschneider et al. ....... | 210/634 |
| 2003/0127394 A1 | 7/2003 | Hotier | |
| 2005/0269268 A1 * | 12/2005 | Hotier ........................ | 210/659 |
| 2006/0006113 A1 * | 1/2006 | Couenne et al. ............. | 210/659 |
| 2008/0041788 A1 * | 2/2008 | Hotier et al. ................ | 210/659 |
| 2008/0121586 A1 * | 5/2008 | Hotier et al. ................ | 210/659 |
| 2008/0237132 A1 * | 10/2008 | Hotier et al. ................ | 210/659 |

FOREIGN PATENT DOCUMENTS

| | | |
|---|---|---|
| EP | 1 325 772 A | 7/2003 |
| FR | 2794663 A1 | 12/2000 |

* cited by examiner

PROCESS AND DEVICE FOR SIMULATED MOVING BED SEPARATION WITH A REDUCED NUMBER OF VALVES AND LINES

FIELD OF THE INVENTION

The invention relates to the field of separation of natural or chemical products which are difficult to separate by distillation. A family of processes and associated devices are used which are known as "chromatographic" or "simulated moving bed" or "simulated counter-current" or "simulated co-current" processes or separation devices which we shall hereinafter term "SMB".

A non-exclusive list of the fields concerned is:
The separation of normal paraffins from branched paraffins, naphthenes and aromatics;
olefin/paraffin separation;
the separation of para-xylene from other isomers of C8 aromatics;
the separation of meta-xylene from other isomers of C8 aromatics;
the separation of ethylbenzene from other isomers of C8 aromatics Beyond the refinery and petrochemicals plant, there are many other applications, including glucose/fructose separation, the separation of positional isomers of cresol, optical isomers, etc

PRIOR ART

SMB chromatographic separation is well known in the art. In general, a simulated moving bed comprises at least three chromatographic zones, advantageously four or five, each of said zones being constituted by at least one bed or a portion of a column and included between two successive supply or withdrawal points. Typically, at least one feed F to be fractionated and a desorbant D (sometimes termed the eluent) are supplied and at least one raffinate R and extract E are withdrawn. The supply and withdrawal points are modified over time, typically shifted towards the bottom of a bed in a synchronous manner.

A plurality of advantageous variations can improve the function of that type of unit by making asynchronous permutations. Put simply, such asynchronous permutations act to compensate for the dead volume(s) of the recirculation pump (s), as indicated in U.S. Pat. No. 5,578,215, to work with a constant recycle rate on the recirculation pump to eliminate jerky flow rates and pressure, as indicated in U.S. Pat. No. 5,762,806, or finally to operate with at least two chromatographic zones each one of which is equivalent to a non-integral number of adsorbant beds. This latter variation, as indicated in U.S. Pat. Nos. 6,136,198, 6,375,839, 6,712,973 and 6,413,419, is known as Varicol®. Naturally, these three variations may be combined.

It should be noted that a multi-way rotary valve placing the incoming and outgoing fluids in communication with the beds disposed in the adsorption column or columns only allows a synchronous type permutation. For asynchronous permutations, a plurality of on-off valves is vital. This technical aspect is described below.

The prior art describes in detail various devices and processes which can carry out the separation of feeds in a simulated moving bed. Particular patents which may be cited are U.S. Pat. Nos. 2,985,589, 3,214,247, 3,268,605, 3,592,612, 4,614,204, 4,378,292, 5,200,075 and 5,316,821. These patents also provide details of the function of a SMB.

SMB devices typically comprise at least one column (and frequently two), adsorbant beds $A_i$ disposed in that column, separated by plates $P_i$ with chamber(s) $C_i$ for distribution and/or extraction of fluids into or from the various beds of adsorbant, and controlled means for sequential distribution and extraction of fluids.

Each plate $P_i$ typically comprises a plurality of distributor-mixer-extractor panels or "DME" supplied via lines or "distribution/extraction manifolds". The plates may be of any type and any geometry, in particular with panels forming adjacent segments of the column section, for example panels with angular segments such as those shown in FIG. 8 of U.S. Pat. No. 6,537,451, which are supplied symmetrically (manifold), or parallel segments such as cutouts in a circumference, as indicated in published patent application US-03/0,127, 394, which are supplied bi-symmetrically. Preferably, the separation column comprises parallel segment type DME plates and bi-symmetrical supplies (in accordance with the invention, the terms "panels" or "segments" shall be used equally). Preferably again, the adsorbant is dense packed. This means that a larger quantity of adsorbant can be used in a given column and increases the purity of the desired product and/or the SMB flow rate.

Distribution over each bed requires flux from the preceding bed (principal fluid moving along the principal axis of the column) to be collected, the possibility of injecting therein an auxiliary fluid or secondary fluid while mixing the two fluids to the best possible extent, or the possibility of removing part of the collected fluid, extracting it to send it out of the device and also to re-distribute a fluid onto the next bed.

To this end, it is possible to use in a plate $P_i$ chambers $C_{i,k}$ for distribution (injection/extraction) which may be separate or be common with the mixing chambers. Plates $P_i$ with one or more chambers are known, either supplied (or exhausted) separately by different fluids at a given time, or supplied (or exhausted) simultaneously and in parallel by the same fluid at a given time. In the first case, the plate is said to have a plurality of distribution networks and in the second case it has a single distribution network. The invention pertains exclusively to a device comprising plates with a single distribution network.

In general, either all of the fluid or principal flux is passed through the column in a manner described in U.S. Pat. No. 2,985,589, or a large part or all of that flux is evacuated as described in the process disclosed in U.S. Pat. No. 5,200,075.

A generic problem with all SMB devices is minimizing the pollution generated by the liquid encountered in the various zones and volumes of the supply and withdrawal circuits for the fluids to/from the plates during modifications to the supply and withdrawal points during operation of the SMB. When during the operating sequence a line, chamber or supply zone for a plate $P_i$ is no longer flushed by a process fluid, it becomes a dead zone in which the liquid stagnates, and only moves again when another process fluid moves in it. Since the nature of SMB requires that this is a different process fluid, the liquid in the dead zone is necessarily displaced by a liquid with a substantially different composition. Mixing or circulation over a short time interval of fluids with substantially different compositions thus introduces a deviation from ideal operation, which proscribes discontinuities in composition.

A further problem may reside in any re-circulation between different zones of the same plate, which thus also induces a deviation from ideal operation.

To overcome these problems linked to re-circulation and dead zones, various techniques are already known in the prior art:

a) flushing of the lines and dead zones by a desorbant or relatively pure desired product has already been proposed. That technique effectively prevents pollution of the desired product during its extraction. However, since the flushing liquid typically has a composition which is very different from the liquid it displaces, this introduces discontinuities in the composition which are prejudicial to ideal operation. This first flushing variation typically carries out "short duration flushes at a high concentration gradient". These flushes are brief to limit composition discontinuity effects.

b) As described in U.S. Pat. No. 5,972,224, another solution consists of passing the majority of the principal flux towards the interior of a column and a minority of that flow towards the exterior, typically 2% to 20% of the flux, via external bypass lines between neighbouring plates. This flush is typically carried out most of the time or continuously, so that the lines and zones are no longer "dead" but are flushed. Such a system with flushing via bypass lines is shown in FIG. 1 of U.S. Pat. No. 5,972, 224 and repeated in a simplified version in FIG. 1 of the present application. Since the bypass lines are designed for a low flow rate, they may as a result be small in diameter, and comprise a small diameter valve, which reduces the cost of the system.

A first advantage of such a system is that the injection and withdrawal circuits for the secondary fluids are flushed with liquid with a composition which is very close to the displaced liquid since firstly, the bypass derives from a neighbouring plate, and secondly, flushing is substantially continuous rather than discontinuous. Further, the flow rates in the bypasses are preferably determined so that the transit rate in each bypass is substantially the same as the rate of advance of the concentration gradient in the principal flux of the SMB. Hence, the various lines and capacities are flushed with a fluid which has a composition which is substantially identical to that of the liquid which is found therein, and the liquid circulating in a bypass is re-introduced at a point where the composition of the principal flux is substantially identical. This second variation can thus carry out "long duration flushes with a small or zero concentration gradient".

A second advantage of this long duration flush system (apart from the injection or withdrawal periods) is that it can remove the effects of possible re-circulation between zones of the same plate due to small pressure drop differences.

Regarding the function of a SMB, the controlled fluid distribution and extraction means of a SMB are typically one of the two following major types of technique:
  either, for each plate, a plurality of controlled on-off valves for supplying or withdrawing fluids, said valves typically being located in the immediate vicinity of the corresponding plate, and in particular comprising, for each plate Pi, at least 4 controlled two-way on-off valves respectively to supply fluids F and D and withdraw fluids E and R;
  or a multi-way rotary valve for supplying or withdrawing fluids over the whole assembly.

The first technique uses two-way valves, which can be mass produced, resulting in increased reliability and a relatively low unit cost. The second technique uses only a single valve, but that single valve is a multi-way valve and necessarily is of special construction, of large dimensions and is extremely complex. Further, this second technology excludes the possibility of asynchronous permutations, as in the Varicol device.

The invention concerns SMB using conventional two-way valves, i.e. using the first of the two techniques described above. In particular, it concerns an improved device for simulated moving bed separation comprising a plurality of two-way on-off valves, but with a reduced number with respect to the prior art. It can be used both for SMB with synchronous permutations and for SMB with asynchronous permutations, for example a Varicol.

BRIEF DESCRIPTION OF THE INVENTION

The invention concerns an improved device for simulated moving bed separation belonging to the major simulated moving bed technique using a plurality of controlled two-way on-off valves, typically standard valves mass produced at low cost to the required high standard (seal/reliability).

One of the essential aims of the invention is to reduce the relative disadvantage of this type of SMB, which is to require a large number of controlled two-way valves. The invention can reduce the number of these valves, while retaining the advantage of being able to provide effective flushing of dead zones of the "long duration at a small or zero concentration gradient" type.

A further aim of the invention is to provide a device which requires a reduced number of two-way valves without the open/close frequency of those valves being increased with respect to the prior art; this along with the reduced number of valves limits the statistical risks of malfunction and thus increases the reliability of the system.

Finally, in a preferred variation of the device, the number of large diameter valves which allow circulation of the principal fluids of the SMB at their nominal flow rate can be further reduced.

The device of the invention may be used in new facilities, but is also compatible with various existing facilities on which it may be installed, by carrying out limited modifications. It is also compatible with various types and geometries of plates Pi, for example plates with angular sector panels or with parallel segments, provided that said plates (or the majority thereof) are of the single distribution network type.

Thus, a means has been discovered which can substantially reduce the number of principal controlled valves, corresponding to the inlets/outlets for fluids for the SMB process: in the prior art, for each plate there is at least one set of 4 principal network valves for supply/extraction of F, D, R, E. This number is further increased if there are more than 4 fluids, for example if there are two raffinates R1, R2 or if a reflux RE is used which is rich in the desired product. In the prior art, the bypass lines, which have a small diameter, are only auxiliary lines which are not used by the fluids F, D, R, E (E1) (E2) (RE) at their nominal supply or withdrawal flow rate.

According to the invention, the column or the principal portion of that column is grouped into superimposed sectors Sk, each sector Sk comprising 2 adsorbant beds and 2 plates, and comprising a bypass line Lk. In contrast to the prior art, the fluids of the SMB use the line Lk at their nominal flow rate and a single set of principal network valves (supply or withdrawal) per column sector is used (rather than per plate as in the prior art), said valves being connected to the bypass line Lk to allow circulation of these fluids via Lk. According to the invention, "plate valves" are also provided, and means for limiting the flow rates of the bypass fluids, but the total number of valves remains substantially reduced, as will be explained below.

Finally, according to a characteristic disposition of the device of the invention, the connections of lines Lk on the column are offset by at most 200 within Sk, to limit the length and volume of lines Lk, and offset by a mean angle in the range 700 to 110° between two neighbouring sectors Sk and Sk+1 so as not to render the column mechanically weak. The plates preferably comprise panels DMEi,j with parallel segments the direction of which varies from plate to plate or per group of 2 plates.

The invention also concerns a process for SMB separation using the device described above, in particular for the separation of para-xylene or meta-xylene from a feed of aromatic hydrocarbons containing 8 carbon atoms.

The invention also concerns the use of the device described above for separating an aromatic from an aromatics cut containing the same number of carbon atoms.

DETAILED DESCRIPTION OF THE INVENTION

The invention will be better understood from the following description, made with reference to FIG. 1 (prior art) and FIGS. 2 to 7 (device or parts of the device of the invention).

To achieve one of the aforementioned aims, the invention thus proposes a device for separating at least one desired compound from a mixture comprising that compound by simulated moving bed adsorption comprising:

at least one column divided into a plurality of adsorbant beds Ai separated by distributor/extractor plates Pi to sequentially supply and extract at least two supply fluids: a feed F and a desorbant D, and at least two withdrawn fluids: a raffinate R and an extract E, Pi being disposed between the bed Ai and the immediately inferior bed Ai+1;

the device also comprising at least one feed network F-Net, a desorbant network D-Net, a raffinate network R-Net and an extract network E-Net, each of these networks being connected to the column via a plurality of intermediate lines comprising controlled two-way isolation valves termed network valves to sequentially supply or withdraw the fluids F, D, R, E;

in which the column is divided over at least the main portion of its height into a plurality of superimposed adjacent sectors Sk, each sector Sk being constituted by a column sector essentially comprising a group of two successive beds of adsorbant and the two distributor/extractor plates Pi which are disposed immediately below said successive beds of adsorbant (Sk comprising exactly 2 beds and 2 plates, and clearly also the sector of the shell of the corresponding column);

each of the distributor/extractor plates Pi of each of the sectors Sk uses a single common network for sequential supply and withdrawal of fluids F, D, R, E;

the plates Pi of each sector Sk are connected together via an external bypass line Lk connected to each plate Pi of Sk via a connector comprising a single controlled two-way isolation valve belonging to plate Pi, termed the plate valve Vi, to sequentially supply or withdraw fluids F, D, R, E to or from Pi;

each of said bypass lines Lk comprises at least one controlled means for limiting the flow circulating in Lk (such as a controlled valve+flow meter+valve control system) which is either installed on line Lk or bypasses around a plate valve Vi of a plate Pi of Sk;

in which the bypass line Lk of each of the sectors Sk is connected to each of the F-Net, D-Net, R-Net and E-Net networks via a single line comprising a single network valve, respectively $V_{Fk}$, $V_{Dk}$, $V_{Rk}$, $V_{Ek}$, for sequential supply or withdrawal of fluid corresponding to F, D, R, E to or from the sector Sk under consideration;

this device comprising at least 2 adjacent superimposed sectors Sk and Sk+1, Sk comprising plates Pi−1 and Pi connected by an external bypass line Lk connected to the column via two connectors respectively comprising the valves of plates $V_i$−1 and $V_i$, and Sk+1 comprising plates Pi+1 and Pi+2 connected by an external bypass line Lk+1 connected to the column via two connectors respectively comprising plate valves $V_i$+1 and $V_i$+2;

and in which the two connectors of Sk on the column have between them an angular offset with respect to the axis of the column which is zero or 20° or less, the two connectors of Sk+1 on the column having between them an angular offset with respect to the axis of the column which is zero or 20° or less, and the connectors of Sk having a mean angular offset in the range 70° to 110° with respect to the connectors of Sk+1.

In contrast to the prior art device, the device of the invention allows the bypass line Lk to be used to circulate fluids F, D, R, E supplied to the SMB and withdrawn from the SMB at the sector Sk via a corresponding single set of network valves, instead of one set of network valves per plate Pi as in the prior art. This substantially reduces the overall number of controlled valves, even when the addition of supplemental valves, namely the plate valves Vi, is taken into account.

The controlled valves cited above: network valves and plate valves Vi, are typically high quality valves (reliability, seal, service life) carrying out the sequential operation of the SMB.

More generally, all of the controlled valves ensuring the sequential function of the SMB: network valves, plate valves Vi, and also the valves of the controlled means for limiting the flow circulating in Lk, must be considered, in accordance with the invention, as the "principal" valves of the SMB, connected to the column and controlled via the system for controlling the sequential function of the SMB (computer, programmable means or other equivalent system).

Certain principal valves for the sequential operation of the SMB were mentioned above as being unique to the invention: Vi for each plate Pi; a single set of network valves $V_{Fk}$, $V_{Dk}$, $V_{Rk}$, $V_{Ek}$ for each sector Sk. However, the scope of the invention encompasses the additional use of other valves such as occasional secondary isolation valves, typically of a far inferior quality, which may or may not be controlled, but not participating in the sequential operation of the simulated moving bed and, for example, being present for the purposes of dismantling any equipment: pump or principal valve used for sequential operation, etc.

Typically, the bypass line Lk, which is used to transmit all of the fluids F, D, R, E at their nominal flow rate, in the device of the invention, is no longer a small auxiliary line as in the prior art, but generally has an internal diameter which is at least equal to the largest diameter of the opening of the network valves connected to Lk to allow the fluids F, D, R, E to circulate without limiting capacity.

Because bypass lines Lk are used which can transport large flows, controlled flow rate limiter means are advantageously used to circulate a small flow as a bypass (typically 2% to 20% of the flow moving in the column). The term "bypass circulation" as used here means that a (small) fraction of the flow moving in the column is withdrawn from a plate and re-introduced into another plate of the same sector Sk. The term "controlled means" typically applies to a controlled valve, typically programmed by a link, starting from information provided by a flow meter. To this end, a flow rate regulating valve may be used which is installed directly on the line Lk.

This valve is thus typically a creeper valve and not an on-off controlled valve (which has only 2 possible positions: fully open, and closed).

However, in a preferred variation of the invention, at least one or preferably each of the bypass lines Lk comprises a controlled means for limiting the flow circulating in Lk, which is not installed directly on Lk but as a bypass around a plate valve Vi of a plate Pi of Sk, on a small secondary bypass lk. This means is generally a controlled valve vi with a smaller diameter opening than that of Vi, for example with a diameter at most 60% or 50% that of Vi, for example in the range 10% to 50% of the diameter of Vi. When an internal flush is to be carried out as a bypass around Lk and this internal bypass flow is to be limited (circulating from one plate of Sk to another plate of Sk), plate valve Vi is closed and the small valve vi bypassing around Vi is opened. Thus, the use of a small secondary bypass lk around one of the plate valves Vi (typically the valve Vi of the lower plate Pi of Sk) allows a smaller opening diameter valve to be used than if the flow limiter means was a valve disposed on the principal bypass line Lk, which has a relatively larger diameter because Lk must allow circulation of fluids F, D, R, E at their nominal flow rate.

According to the invention, the connector comprising Vi must be interpreted as not including the small secondary bypass lk around Vi, nor the small valve vi disposed on lk. This connector thus comprises a single valve Vi allowing circulation of the principal fluids F, D, R, E.

A sector Sk must be defined in the case of the column bottom. Typically, there is no plate Pn below an adsorbant bed An disposed at the column bottom as there is no need to distribute fluids into an immediately inferior bed. Further, in accordance with the invention, in this case it is assumed that the missing plate Pn is replaced by the lower outlet line from the column, typically connected either to the inlet to the same column, via a re-circulation pump, or to the head of a second separation column.

Preferably, the entire column (with the exception of the head plate, excluded by definition from the term "sector"), is constituted by superimposed adjacent sectors Sk.

It may also be substantially constituted by a combination of sectors with 2 beds and 2 plates and one or more sectors with 3 beds and 3 plates. Finally, in a variation which is not preferred, it is also possible to use sectors Sk with 2 beds and 2 plates of the invention and one or more individual plates Pi supplied in accordance with the prior art, as shown in particular in FIG. 1.

The invention described above in the case of 4 networks of fluids F, D, R, E may also be used in a similar manner when there are not 4 but 5 or 6 fluid networks, for example by using 2 raffinates R1, R2 and/or a reflux RE of product rich in the desired product. Thus, there are 5 or 6 network valves per sector Sk and line Lk.

The device of the invention can also limit the lengths of the external bypass lines Lk and Lk+1 since the connecting connectors (or taps, a connector also being a tap onto the column) of each of these lines are superimposed or have a small angular offset (at most 20°). This is favourable as regards limiting the internal volumes of lines which have to be flushed when the supply/extraction fluid is changed. However, due to a large mean angular offset in the range 70° to 110° between the connectors of two adjacent superimposed sectors Sk and Sk+1, mechanical weakening of the column by an accumulation of substantially superimposed taps on the same generatrix of the column is avoided.

In accordance with the invention, the term "orientation" of a connector or tap applies to the orientated straight line starting from the centre of the plate on the axis of the column and directed towards this connector (at its point of connection with the column). By definition, the angular offset between two connector orientations (for two different plates) is the smallest angle formed by the orientations of the connectors of these two plates, projected on the horizontal reference plane. It is thus an angle which is always in the range [00-180°]. The mean orientation of two connectors (for an assembly of two different plates) having an angular offset of an angle alpha of <180°, is by definition the median orientation corresponding to an angular offset of alpha/2 with respect to two orientations of the connectors under consideration. The mean angular offset between the connectors of two sectors Sk and Sk+1 is the angular offset of the mean orientations of the connectors of these two sectors.

Typically, the whole column with the exception of the head of the column comprising the head plate and optionally the column bottom comprising the lower bed and/or lower plate is constituted by a plurality of superimposed 2-plate sectors in which the two connectors of the same sector Sk has an angular offset with respect to the axis of the column of zero or 20° or less, and any two superimposed adjacent sectors have between them a mean angular offset of their connectors in the range 70° to 110°.

The lower plate may also belong to a sector Sk with a connection of Lk at the lower point to the column outlet line (and no longer to the column) and thus preferably has the same angular offset characteristics between its two taps (zero or 20° or less) as well as a mean angular offset of these taps with respect to those of the immediately superior sector Sk−1 which is typically in the range 70° to 110°.

Preferably, the connectors of any sector Sk have between them a substantially zero angular offset and any two adjacent superimposed sectors have between them a mean angular offset of their connectors of substantially 90°. In this case, the bypass lines Lk are typically parallel to one generatrix of the column and thus of minimum length.

In accordance with a preferred characteristic of the invention, the angular offsets of the taps are used to change the orientation of the parallel segment panels DMEi,j typically composing the plates. This change of direction of the parallel segment panels (or panel orientation) can limit local heterogeneities of fluid circulation due to the geometry of the plates and their supply/extraction system: by avoiding a uniform orientation of the panels, and in contrast by changing their orientation, preferably by an angle close to 90°, a cumulative effect of circulation heterogeneities along the column is avoided. As an example, a smaller circulation at a local zone of a plate will be partially or totally compensated for by an increased zone of circulation of a lower plate located in the same portion of the column. This tends to equalize the adsorption fronts of products on a section of the column.

In accordance with the invention, the term "direction of the parallel segments" applies to the straight line, not orientated in one or the other direction, located in a horizontal reference plane which is parallel to the sectors under consideration and passes through the column axis. By definition, the angular offset between two directions (or orientations) of parallel segment panels (of two different plates) is the smallest angle formed by the directions of the parallel segments of these two plates, projected onto the same horizontal reference plane. It is thus an angle which is always included in the interval [0°-90°].

The mean direction (or orientation) of the parallel segments of two different plates wherein one of the directions is offset by an angle alpha of <90° with respect to the other is by definition the median direction, corresponding to an offset angle of alpha/2 with respect to the two directions under consideration.

Thus, in accordance with a first design variation of the plates of the device, each plate Pi of a sector Sk is subdivided into a plurality of panels DMEi,j with sectors parallel to a direction connected to a single connector (EMi) to supply the supply fluids and withdraw the extraction fluids and for each plate of a sector Sk, the directions of the parallel segment panels of the plates of a single sector Sk have an angular offset of zero or 20° or less, and the mean direction of the panels with parallel segment panels of a sector Sk has an angular offset in the range 70° to 90°, limits included, with respect to that of the panels of a neighbouring sector Sk+1 or Sk−1.

The direction of the parallel segments of this plate preferably have a constant angular offset with the connector connected to this plate, this constant offset typically being either substantially zero or substantially 90°.

In accordance with this variation, the direction of the panels DMEi,j with parallel segments of the plates of a single sector Sk are thus substantially similar or identical (with at most 20° of offset). In contrast, the mean directions of the parallel segment panels of the plates change by an angle in the range 70° to 90° when passing from one sector Sk to an adjacent sector. Thus, every two plates there is a large change in direction (close to 90°) of panels (sector by sector).

In a second variation in the design of the plates and device, each plate Pi of a sector Sk is subdivided into a plurality of segments parallel to one direction, connected to a single connector to supply the supply fluids and extract the withdrawn fluids and for each assembly of two superimposed adjacent plates belonging to the same sector Sk or to two superimposed sectors, the direction of the parallel segment panels of one of the two plates has an angular offset in the range 70° to 90°, limits included, with the direction of the parallel segments of the other plate.

In this variation, the directions of the parallel segments of the two plates of a single sector Sk are substantially offset by 90°, and this same offset exists when passing from the plate below Sk to the adjacent lower plate belonging to the lower sector Sk+1. The changes in direction of the parallel segments thus in this case occur at each plate and no longer at each group of 2 plates (at each sector), which increases the changes in direction of the sectors. In contrast, since the 2 connectors have a zero or small angular offset within the same sector, this change in direction then necessitates two different designs of plate, with segment orientations offset by 90°, as will be explained when the Figures are described.

Typically, the bypass line Lk has an internal diameter at least equal to the largest opening diameter of the network valves connected to Lk. Thus, the diameter of Lk does not constitute a limitation to the flow compared to the opening diameter of the network valves connected directly to Lk.

As already mentioned, the SMB may function with a reflux RE, including the extract, or typically rich in the desired product obtained by distilling the extract to eliminate the desorbant (comprising more than 50%, or even 90% or even 99% of the desired product). Preferably, the device of the invention then comprises a sequential supply network RE-Net of the reflux RE, this network being connected to each of the sectors Sk via a single large diameter line. Thus, the reflux network is connected in a manner identical to those of the other process fluids F, D, R, E.

In analogous manner, the SMB may also function with a sequential withdrawal of a second raffinate r2, and in this case the device of the invention preferably comprises a network R2-Net connected to each of the sectors Sk via a single large diameter line comprising a single network valve which is also of large diameter. Thus, the second raffinate network is connected in a manner identical to those of the other process fluids F, D, R, E, (RE).

The invention also concerns a separation process using the device described above, in which during a cycle each line Lk is used sequentially to circulate the fluids F, D, R, E at their nominal flow rate to or from each of the plates Pi of Sk via, in series, the plate valve Pi and one of the network valves $V_{Fk}$, $V_{Dk}$, $V_{Rk}$, $V_{Ek}$ and in which Lk is used by each of the fluids F, D, R, E over the whole of its length during one cycle.

In general, an internal flush of at least a portion of each of the bypass lines Lk is carried out when no network valve connected to Lk is open and all internal flushing of Lk is stopped when a network valve connected to Lk is open.

Preferably, an internal flush of Lk is carried out from plate Pi located in an upper position in Sk and towards the plate Pi+1 or Pi+2 which is located in a lower position in Sk, over all time periods when Sk is not connected to one of the fluid networks, and which is immediately before a period when one of the network valves connected to Sk is open to supply or withdraw one of the fluids to or from the plate Pi. This internal flush results in opening of Vi in the period preceding a supply or withdrawal period for a plate Pi (which also requires opening Vi) and avoids opening or closing Vi between these consecutive periods. The reduction in the number of movements of the valves reduces wear of these valves and increases the reliability of the device and the associated process.

In general, internal flushes are carried out of at least two and usually all the bypass lines Lk. Typically, the internal flush takes place over at least 20%, usually at least 40% or even at least 50% of the time.

The invention can carry out all sorts of chromatographic separations, in particular a process for separating para-xylene, as a product, from a feed of aromatic hydrocarbons containing 8 carbon atoms, or a process for separating meta-xylene, as a product, from a feed of aromatic hydrocarbons containing 8 carbon atoms.

In general, it allows the device described above to be used to separate any aromatic hydrocarbon from a feed of aromatic hydrocarbons containing the same number of carbon atoms.

DESCRIPTION OF FIGURES AND OPERATION OF DEVICES SHOWN

The invention will be readily understood from the accompanying drawings and description in which:

FIG. 1 is a diagrammatic representation of part of a prior art SMB device, with the corresponding network valves;

FIG. 2 diagrammatically shows part of a SMB device of the invention, comprising sectors Sk with 2 beds and 2 plates, with the corresponding network valves, plate valves and bypass flow rate limiting valves and having F-Net; D-Net; R-Net and E-Net and also Sk wherein: F-Net links all the lines "F", D-Net links all the lines "D", R-Net links all the lines "R", E-Net links all the lines "E".

FIGS. 3a and 3b diagrammatically show an intermediate sector and the bottom column sector of a device of the invention in the case of sectors Sk with 2 beds and 2 plates;

FIG. 4 diagrammatically shows an intermediate sector Sk with 2 beds and 2 plates in the case in which the flow limiting means of Lk is a regulating valve disposed on Lk;

Figure 1:
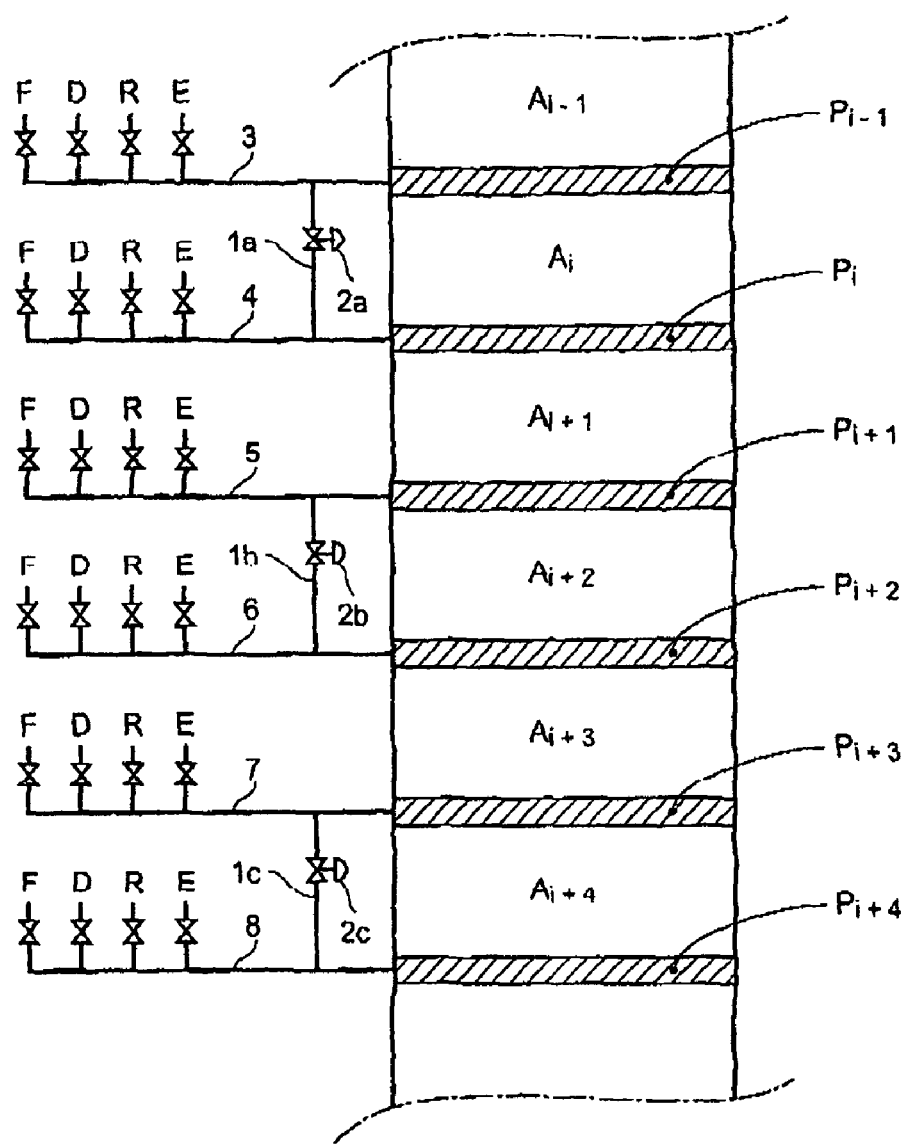

We refer now to FIG. 1, representing part of a chromatographic column of a prior art SMB. Each of the beds of adsorbant Ai−1, Ai, Ai+1, Ai+2, Ai+3, Ai+4 is disposed above a plate Pi−1, Pi, Pi+1, Pi+2, Pi+3, Pi+4, and each of said plates is connected via a line, respectively 3, 4, 5, 6, 7, 8 to each of 4 fluid networks F, D, R, E via a valve (no reference). There are thus 4 principal valves per plate. Further, the plates are connected in pairs via a bypass line 1*a*, 1*b*, 1*c* comprising a small diameter valve, respectively 2*a*, 2*b*, 2*c*, to allow the passage of a limited bypass flow: 2% to 20% of the flow circulating in the column. In total, then, there are 4 principal valves and on average 0.5 small diameter valves (one for 2 plates) for each plate Pi, giving an average of 4.5 valves per plate.

The function of a SMB using such a column is well known to the skilled person. Typically, valve 2*a*, 2*b* or 2*c* of a bypass line is open when no fluid F, D, R, E is supplied or withdrawn from one of the 2 plates connected via the bypass line (bypass temporarily in service). In contrast, valve 2*a*, or 2*b*, or 2*c* of a bypass line is closed when one of fluids F, D, R, E is supplied or withdrawn to/from one of the 2 plates connected via the bypass line (bypass temporarily out of service).

Figure 2:
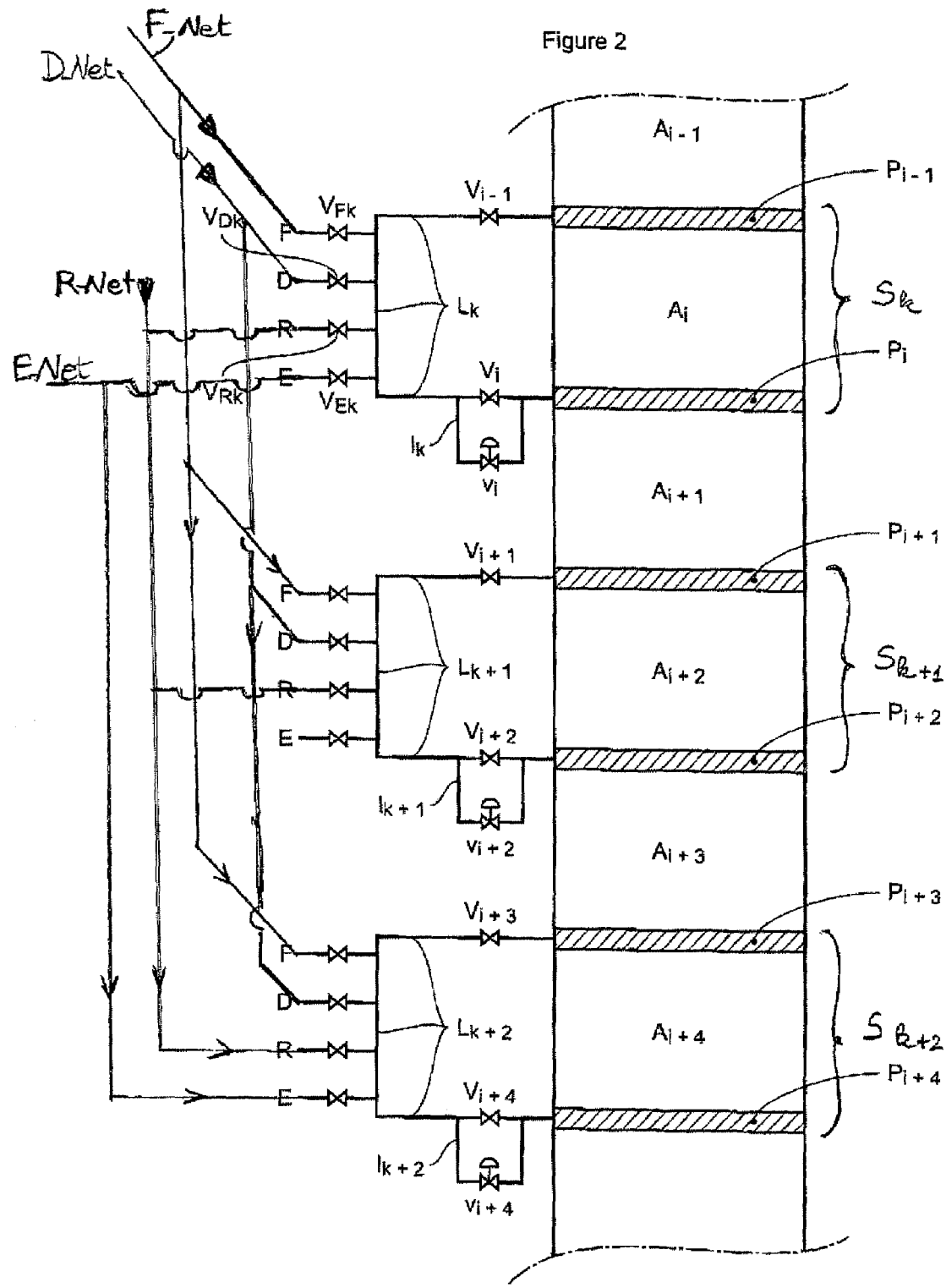

FIG. 2 shows part of a column of a device of the invention comprising 3 sectors Sk, Sk+1, Sk+2, each comprising 2 beds of adsorbant and 2 plates located immediately below. The 2 plates of each sector are connected via a bypass line, respectively Lk, Lk+1, Lk+2 which is suitable for circulating fluids F, D, R, E at their nominal flow rate. Each bypass line is connected to a set of 4 network valves for supply and withdrawal of fluids. In contrast to the prior art, this set of 4 valves supplies not 1 but 2 plates.

Thus, for the first sector Sk, there are 4 network valves $V_{Fk}$, $V_{Dk}$, $V_{Rk}$, $V_{Ek}$ supplying both Pi−1 and Pi.

Each plate is also connected to a corresponding bypass line Lk or Lk+1 or Lk+2 via a connector (corresponding to the horizontal part of the line in the Figure) comprising a single two-way controlled isolation valve belonging to the plate, termed a plate valve: Vi−1, Vi, Vi+1, Vi+2, Vi+3, Vi+4. Each lower plate valve of a sector: Vi, Vi+2, Vi+4 also has a small secondary bypass line ik, $lk_{+1}$, $Ik_{+2}$ provided with a valve which is typically of small diameter: vi, vi+2, vi+4.

In total, for each sector of 2 plates, there are 4 network valves, 2 plate valves and a small diameter valve in the secondary bypass, namely 7 valves, giving an average of 3.5 valves per plate.

The device operates as follows:

For the sector Sk, for example, when in a given period, one of the fluids F, D, R, E is to be supplied or withdrawn to/from the plate Pi−1, the corresponding network valve $V_{Fk}$, $V_{Dk}$, $V_{Rk}$, $V_{Ek}$ is opened as well as the plate valve Vi−1. The other network valves of the sector Sk are thus closed, as well as Vi and the small secondary bypass valve vi.

When in another period one of the fluids F, D, R, E is to be supplied to or withdrawn from the plate Pi, the corresponding network valve $V_{Fk}$, $V_{Dk}$, $V_{Rk}$, $V_{Ek}$ and the plate valve Vi are opened. The other network valves of sector Sk are thus closed, as well as Vi−1. The small secondary bypass valve vi may remain closed.

When in a third period fluids F, D, R, E are neither to be supplied to nor withdrawn from plates Pi−1 and Pi, the network valves $V_{Fk}$, $V_{Dk}$, $V_{Rk}$, $V_{Ek}$ are closed. A limited bypass flow is then circulated in the line Lk (withdrawn from Pi−1 and injected into Pi), by opening Vi−1, closing Vi and opening the small secondary bypass valve vi. Thus, a small bypass flow is ensured via lk. vi is typically a regulating valve (progressive opening) piloted by regulating the flow rate from a flow meter, not shown.

The other sectors Sk+1, Sk+2, function in an analogous manner.

Figure 3A:
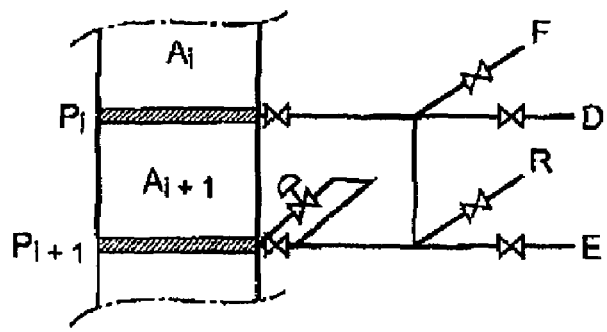
Figure 3B:
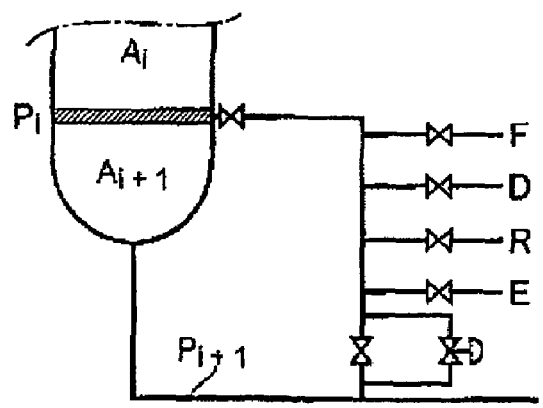

FIGS. 3*a* and 3*b* diagrammatically show a sector with 2 beds and 2 plates. FIG. 3*b* shows such a sector at the column bottom. In accordance with the invention, it is assumed that the line denoted Pi+1 by definition replaces the plate located below the bed Ai+1, this plate being absent from the column bottom.

Figure 4:
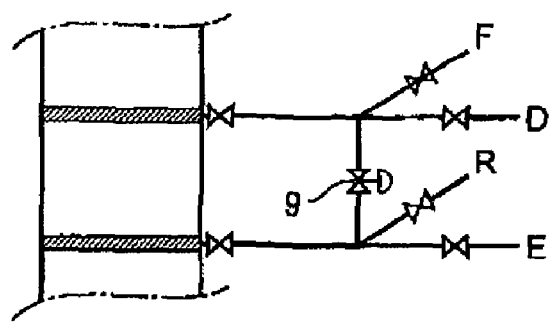

FIG. 4 shows a sector Sk with 2 beds and 2 plates in which the bypass flow rate limiting means does not comprise a secondary bypass with a valve vi, but a larger diameter valve 9 disposed on the line Sk itself (with associated flow rate measurement means, not shown).

FIGS. 5*a*, 5*b*, 5*c* and 5*d* show top views of various embodiments of a plate Pi with parallel segments panels DMEi,j with their supply/extraction network. The present invention is not concerned with the geometry of the branches of this network.

Figure 5A:
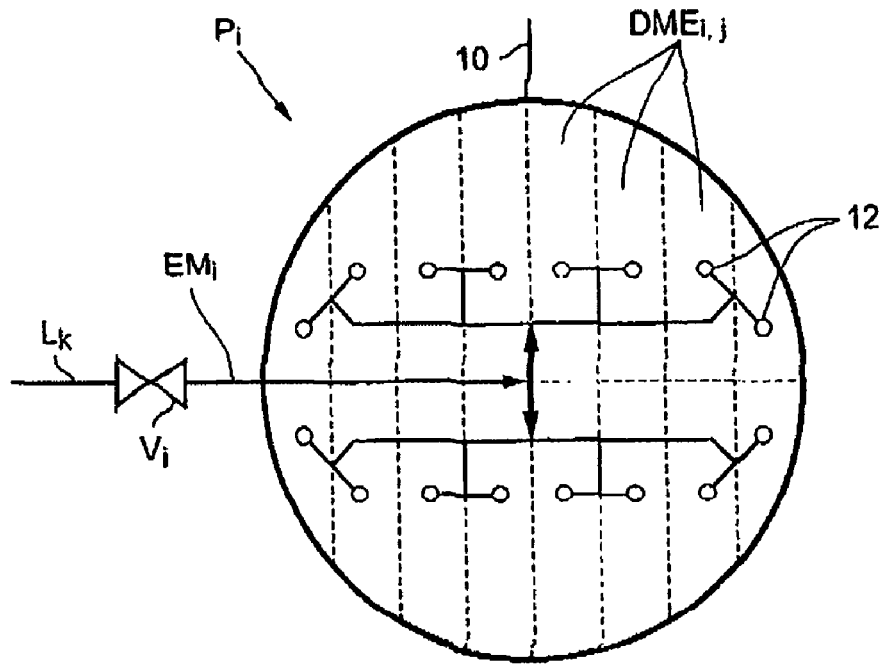
FIGS. 5a, 5b, 5c and 5d show four plate variations Pi with parallel segments with their supply/extraction network.
Figure 5B:
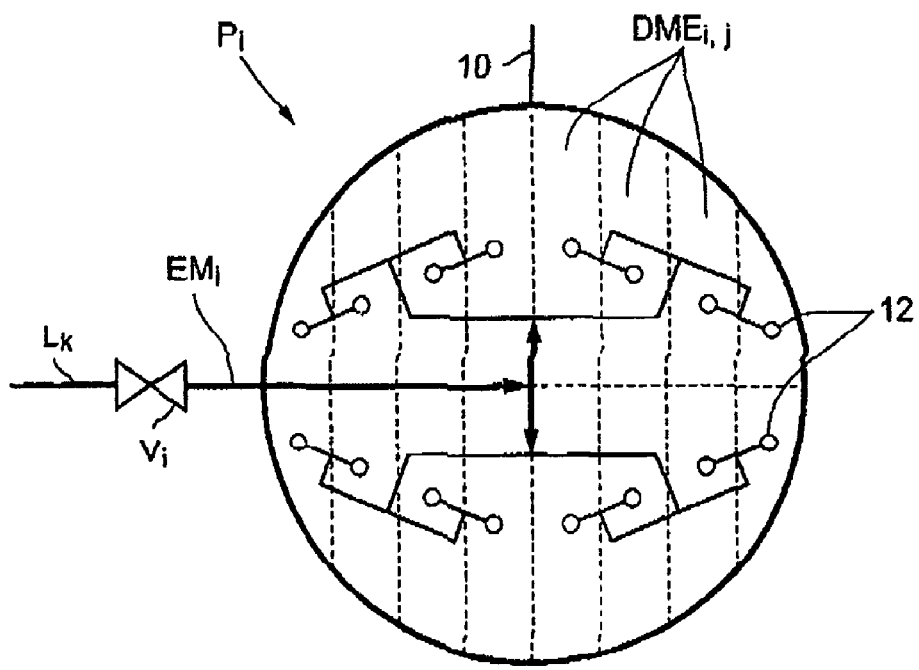
Figure 5C:
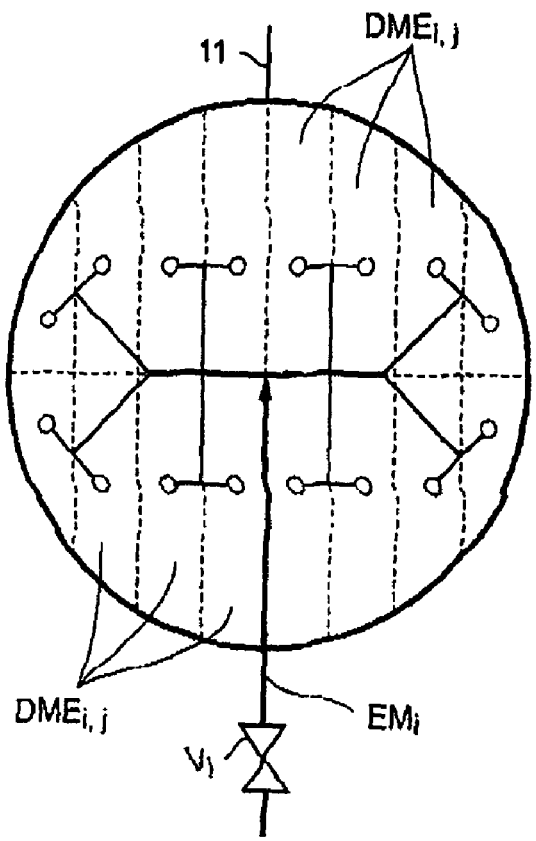

For each of the plates corresponding to FIGS. 5*a*, 5*b* and 5*c*, the single connector EMi connected to the supply/extraction process fluids network enters the column radially to connect, via a radial line, to the centre of the column where a first division into two is carried out. A series of successive subdivisions can individually supply all of the panels DMEi,j to supply and withdraw the SMB fluids in a regular manner over the whole section of the plate.

Figure 5D:
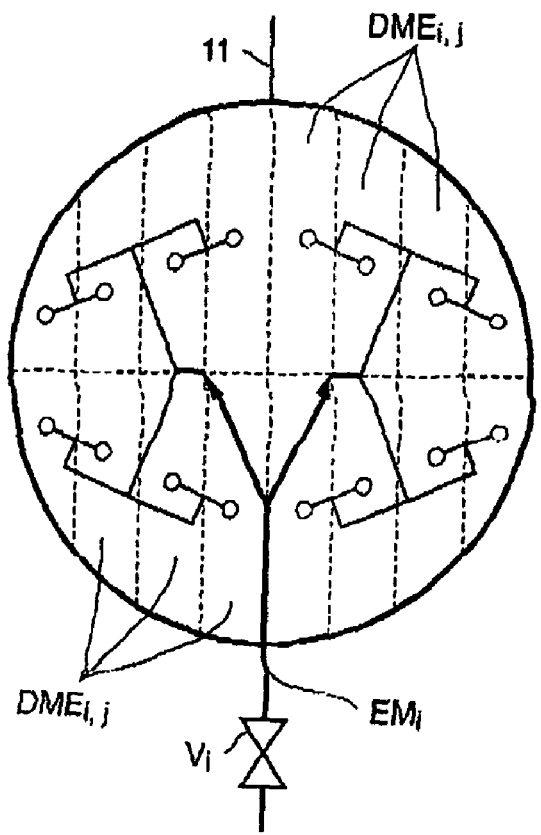

For the plate of FIG. 5*d*, the radial line is subdivided more upstream and does not pass via the centre of the column, which means that a central strut can be installed to support the plates and the adsorbant bed located above the plate.

For the plates of FIGS. 5*a* and 5*b*, the panels DMEi,j extend perpendicular to the connector EMi, parallel to one and the same direction indicated by the non orientated straight line 10. This direction of the parallel segments has an angular offset of 90° with respect to the connector EMi.

In contrast, for the plates of FIGS. 5*c* and 5*d*, the panels DMEi,j extend parallel to the connector EMi and to a direction indicated by the non orientated straight line 11. This direction of the parallel segments thus has a zero angular offset with respect to the connector EMi.

The branches of the single common network for sequential supply and withdrawal of the process fluids can be carried out in a variety of manners. The networks of the plates of FIGS. 5*a* and 5*c* comprise both divisions into two, for example upstream of the terminal ends 12 for connection to the panels, and also the raked subdivisions.

The network of plates of FIGS. 5*b* and 5*d* exclusively comprise successive divisions into two. It is also possible to use divisions such as those disclosed in U.S. Pat. No. 5,938,333.

In general, the dimensions of the lines decreases with the branches, but it is also possible to have parts of the network with lines with the same diameter, and divisions into two with a reduction in diameter on one or two downstream branches, etc. The scope of the invention also encompasses supplying each panel DMEi,j via two terminal ends 12 rather than just one.

Figure 6A:
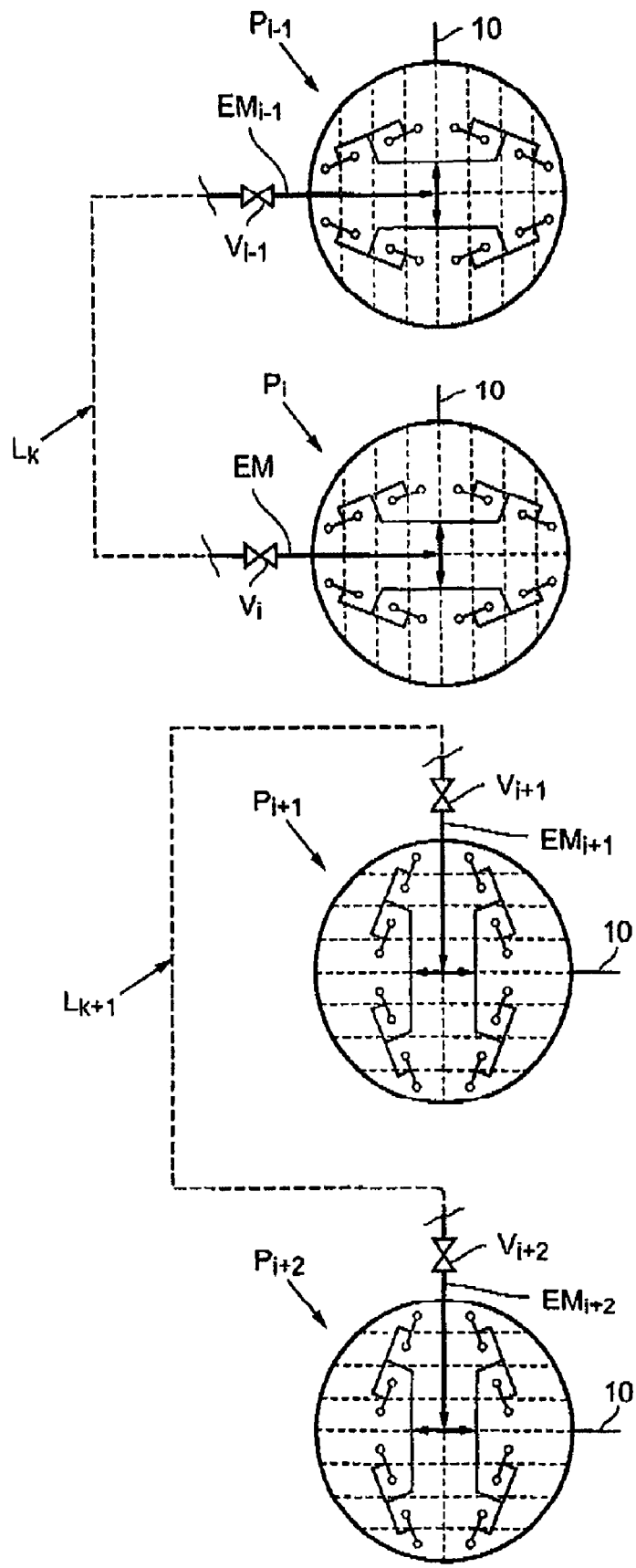
FIGS. 6a and 6b show two variations in the disposition of 4 successive adjacent plates corresponding to two sectors Sk and Sk+1.

FIG. 6*a* shows a first variation in the disposition of 4 adjacent superimposed plates corresponding to two sectors Sk and Sk+1. In this variation, all the plates have the design of FIG. 5*b*, all of the parallel segment panels DMEi,j of one plate being perpendicular to the single connector EMi corresponding to this plate, and thus having an angular offset of 90° with this connector.

The connectors of plates Pi−1 and Pi belonging to the same sector Sk are superimposed and thus have an angular offset of zero. For this reason, the line Lk shown as a dotted line is typically of minimum length and is easy to install as it does not have to wind around the column.

The connectors of plates Pi+1 and Pi+2 belonging to the same immediately interior sector Sk+1 are also superimposed and thus also have a zero angular offset. For this reason, the line Lk+1 shown in dotted lines is also typically of minimum length and is easy to install as it does not have to wind around the column.

The connectors of Sk+1 are, in contrast, offset by 90° with respect to those of Sk. This is also the case for the directions of the parallel segment panels of the plates of Sk+1 which are offset by 90° with respect to those of the plates of Sk. Thus, there is an angular offset of 90° of the parallel segments, of every two plates, i.e. sector by sector. This disposition can avoid or limit the accumulation of fluid circulation heterogeneities in the column section because of the imperfectly homogeneous nature of the supply/extraction system. It tends to regularize the adsorption fronts in the various points of the column section compared with a disposition with all of the plates directly superimposed, resulting in an accumulation of heterogeneities due to each new plate.

The variation in the disposition of the 4 adjacent Superimposed (neighbouring) plates of FIG. 6a can thus produce both a typically minimum length for the bypass lines Lk, Lk+1 which is easy to install, but also avoid or limit the accumulation of circulation heterogeneities in the column. Finally, it can avoid an accumulation of taps on one generatrix of the column the connectors being offset by 90° at each new sector. This is favorable for the mechanical behaviour of the column, which is not weakened.

Figure 6B:
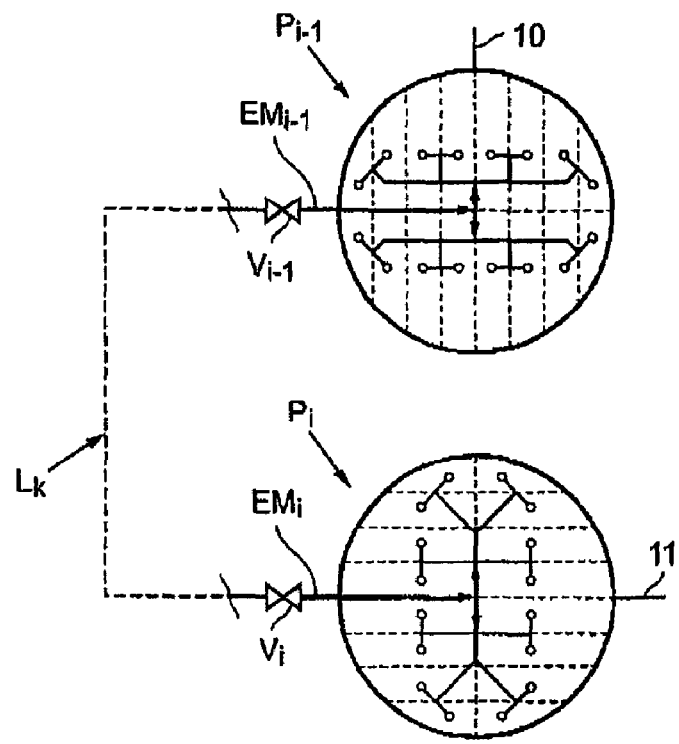
Figure 6B:
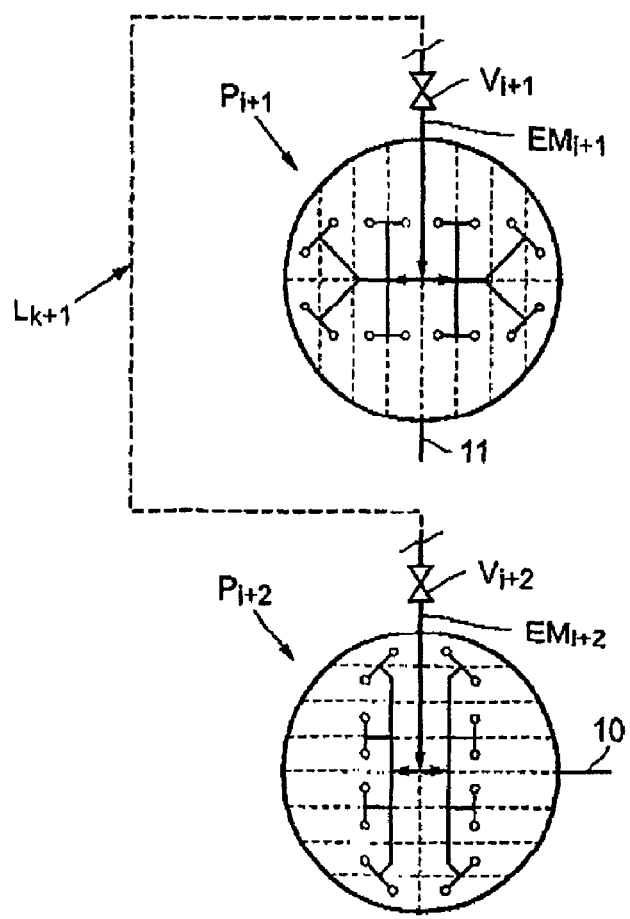

FIG. 6b shows another variation in the disposition of 4 successive adjacent plates corresponding to two sectors Sk and Sk+1. In this variation, there is an angular offset of 90° in the direction of the parallel segment panels of a plate to that of the parallel segment panels of one or the adjacent plate (closest plate(s)), i.e. plate by plate and not sector by sector. This further augments the limitation in the accumulation of circulation heterogeneities in the column.

The two connectors (taps) of one sector Sk or Sk+1 remain superimposed to preserve the advantage of bypass lines typically with a minimum length, and easy to install. This is achieved by the alternating use of two types of plates with different distribution networks: one type in accordance with the design of FIG. 5a (for Pi−1 and Pi+2) and one type in accordance with the design of FIG. 5c (for Pi and Pi+1).

This variation thus allows a more frequent alternation of plates with the change in orientation of the parallel segments, in contrast to using 2 different types of plates. It preserves the advantage of bypass lines which are typically of minimum length and which are easy to install.

Best Implementation

The best implementation of the invention is a SMB wherein the column or columns are essentially constituted by sectors Sk with 2 beds and 2 plates, with the exception, by definition, of the column head comprising the head plate. The sectors Sk include the small secondary bypass lines lk provided with small diameter valves vi. In such a device, by way of example 24 beds and 24 plates (for example 2 columns in a loop of 12 beds and 12 plates each), there are 6 sectors Sk per column, i.e. a total of 12. Thus, to control the SMB, only 24 plate valves are needed, and 4×12=48 network valves (4 for each of the 12 sectors Sk which are required), i.e. 72 principal valves to which 12 small regulation valves vi must be added (secondary bypass), i.e. a total of 84 valves, which represents an average of 3.5 valves per plate.

In the prior art corresponding to FIG. 1, the equivalent SMB requires 4×24=96 principal valves (4 valves per plate) and 12 reduced diameter valves, i.e. a total of 108 valves, and 4.5 valves per plate.

The plates of the preferred embodiment of the device and their parallel segments are offset in pairs by 90° (sector by sector, without changing the plate geometry) as shown in FIG. 6a, or are offset one by one by 90° (plate by plate, with a change in plate geometry), as shown in FIG. 6b, which regularizes the flow of fluids in the column and reduces the volume of the principal external bypass lines Lk which do not need to wind about the column, without weakening the column by an accumulation of superimposed taps (connectors).

The device of the invention as described may be used for any process for chromatographic separation, in particular to separate an aromatic hydrocarbon from a feed of aromatic hydrocarbons essentially containing 8 carbon atoms and including that hydrocarbon.

In particular, it may be used to separate para-xylene from an aromatic cut essentially composed of C8 hydrocarbons, using toluene or para-diethylbenzene as a desorbant and a zeolite as an adsorbant as described, for example, in FR-2 789 914. It may also be used to separate meta-xylene from an aromatic C8 cut, using toluene or tetraline as a desorbant and an adsorbant such as that described in U.S. Pat. No. 5,900,523 and patent applications FR-05/52.485 and FR-05/52.486.

It may also be used to separate one or more normal paraffins (separated from the remainder of the hydrocarbons) from a mixture of hydrocarbons, in particular paraffinic or paraffinic and naphthenic, for example using normal butane or normal pentane as the desorbant (optionally isooctane as in inert diluent) and a 5A zeolite as the adsorbant.

Finally, it may be used to separate at least one olefin from a hydrocarbon cut comprising said hydrocarbon, under conditions known in the art, for example using an X zeolite exchanged with calcium.

The invention is not limited to the above description and to carry it out, the skilled person is at liberty to employ any other characteristic technique which is known in the art.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 07/01.772, filed Mar. 9, 2007 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A device for separating at least one desired compound from a mixture comprising said compound, by simulated moving bed adsorption comprising:
   at least one column divided into a plurality of adsorbant beds Ai separated by distributor/extractor plates Pi for sequential supply and extraction of at least two supply fluids: a feed F and a desorbant D, and at least two withdrawn fluids: a raffinate R and an extract E, Pi being disposed between the bed Ai and the immediately inferior bed Ai+1;

the device also comprising networks of fluids, i.e. at least a feed network F-Net, a desorbant network D-Net, a raffinate network R-Net and an extract network E-Net, each of said networks being connected to the column via a plurality of lines comprising two-way controlled isolation valves, termed network valves, for sequential supply or withdrawal of said fluids;

in which the column is divided, over at least the major portion of its height, into a plurality of superimposed adjacent sectors Sk, each sector Sk essentially being constituted by a column sector essentially comprising two successive beds of adsorbant and the two distributor/extractor plates Pi which are disposed immediately below said successive beds of adsorbant;

each of the distributor/extractor plates Pi of each of the sectors Sk is a single common network for sequential supply and withdrawal of fluids F, D, R, E;

the plates Pi of each sector Sk are connected together via an external bypass line Lk connected to each plate Pi of Sk via a connector (EMi) comprising a single two-way controlled isolation valve belonging to the plate Pi, termed the plate valve Vi, for sequential supply or withdrawal of fluids F, D, R, E from Pi;

each of said bypass lines Sk comprises at least one controlled means for limiting the flow rate circulating in Lk, which is either installed on the line Lk or in a bypass around a plate valve Vi or a plate Pi of Sk;

in which the bypass line Lk of each of the sectors Sk is connected to each of the networks F-Net, D-Net, R-Net and E-Net via a single line comprising a single network valve, respectively $V_F, V_D, V_R, V_E$, for sequential supply or withdrawal of the corresponding fluid F, D, R, E to or from the sector Sk under consideration;

said device comprising at least two superimposed adjacent sectors Sk and Sk+1, Sk comprising the plates Pi−1 and Pi connected via an external bypass line Lk connected to the column via two connectors respectively comprising the plate valves $V_i-1$ and $V_i$, and Sk+1 comprising the plates Pi+1 and Pi+2 connected via an external bypass line Lk+1 connected to the column via two connectors respectively comprising the plate valves $V_i+1$ and $V_i+2$, in which the two connectors of Sk on the column have between them an angular offset with respect to the axis of the column which is zero or 20° or less, the two connectors of Sk+1 on the column have between them an angular offset with respect to the axis of the column which is zero or 20° or less, and the connectors of Sk have with the connectors of Sk+1 a mean angular offset in the range 70° to 110°.

2. A device according to claim 1, in which the whole column, with the exception of the column head comprising the head plate and optionally the column bottom comprising the lower bed and/or the lower plate, is constituted by a plurality of superimposed sectors of two plates, in which the two connectors of a single sector Sk have between them an angular offset with respect to the axis of the column of zero or 20° or less, and any two adjacent superimposed sectors have between them a mean angular offset of their connectors in the range 70° to 110°.

3. A device according to claim 1, in which the connectors of any sector Sk have between them an angular offset of substantially zero, and any two adjacent superimposed sectors have between them a mean angular offset of their connectors of substantially 90°.

4. A device according to claim 1, in which each plate Pi of a sector Sk is subdivided into a plurality of panels DMEi,J with segments parallel to one direction connected to a single connector (EMi) to supply the supply fluids and extract withdrawal fluids and in which for each plate of a sector Sk, the directions of the parallel segment panels of the plates of a single sector Sk have between them an angular offset of zero or 20° or less, and the mean direction of the parallel segment panels of the plates of a sector Sk has an angular offset in the range 70° to 90°, limits included, with respect to that of the panels of a neighbouring sector Sk+1 or Sk−1.

5. A device according to claim 4, in which each of said bypass lines Lk comprises at least one controlled means for limiting the flow circulating in Lk, which is installed as a bypass about a plate valve Vi of a plate Pi of Sk.

6. A device according to claim 5, in which said means for limiting the flow circulating in Lk installed as a bypass around said plate valve Vi comprises a controlled valve with a smaller diameter opening than that of Vi.

7. A device according to claim 1, in which each plate Pi of a sector Sk is subdivided into a plurality of panels DMEi,J with segments parallel to one direction, connected to a single connector (EMi) for supply of supply fluids and extraction of withdrawal fluids, in which for each assembly of two superimposed adjacent plates belonging to a single sector Sk or to two superimposed sectors, the direction of the parallel segments of one of the plates has an angular offset in the range 70° to 90°, limits included, with the direction of the parallel segments of the other plate.

8. A device according to claim 1, in which the bypass line Lk has an internal diameter equal to at least the largest opening diameter of the network valves connected to Lk.

9. A device according to claim 1, in which the whole column with the possible exception of the column head comprising the head plate is constituted by said adjacent superimposed sectors Sk, the column comprising a lower outlet line assimilated to a plate Pn corresponding to the lower bed of adsorbant An.

10. A device according to claim 1, in which each of said bypass lines Lk comprises at least one controlled means for limiting the flow circulating in Lk, which is installed as a bypass about a plate valve Vi of a plate Pi of Sk.

11. A device according to claim 10, in which said means for limiting the flow circulating in Lk installed as a bypass around said plate valve Vi comprises a controlled valve with a smaller diameter opening than that of Vi.

* * * * *